(12) United States Patent
Li et al.

(10) Patent No.: US 9,039,622 B2
(45) Date of Patent: May 26, 2015

(54) IMAGE GENERATION SYSTEM

(71) Applicant: NATIONAL TAIWAN UNIVERSITY, Taipei (TW)

(72) Inventors: Pai-Chi Li, Taipei (TW); Bao-Yu Hsieh, Taipei (TW)

(73) Assignee: National Taiwan University, Taipei (TW)

( * ) Notice: Subject to any disclaimer, the term of this patent is extended or adjusted under 35 U.S.C. 154(b) by 50 days.

(21) Appl. No.: 13/803,657

(22) Filed: Mar. 14, 2013

(65) Prior Publication Data

US 2014/0200454 A1  Jul. 17, 2014

(30) Foreign Application Priority Data

Jan. 16, 2013 (TW) .............................. 102101627 A

(51) Int. Cl.
*A61B 8/00* (2006.01)
*A61B 5/00* (2006.01)
*A61B 8/08* (2006.01)

(52) U.S. Cl.
CPC ................. *A61B 8/44* (2013.01); *A61B 8/4416* (2013.01); *A61B 5/0095* (2013.01); *A61B 8/5261* (2013.01)

(58) Field of Classification Search
CPC ...... A61B 8/44; A61B 8/4483; A61B 5/0095; A61B 8/5261
USPC .................................................. 600/443, 437
See application file for complete search history.

(56) References Cited

PUBLICATIONS

Bao-Yu Hsieh et al., "All-Optical Transducer for Ultrasound and Photoacoustic Imaging by Dichroic Filtering." 2012 IEEE International Ultrasonics Symposium Proceedings, pp. 1410-1413.*
Bao-Yu Hsieh et al., "All-Optical Generation and Detection of Acoustic Waves for Intravascular Ultrasound and Photoacoustic Imaging." 2011 IEEE International Ultrasonics Symposium Proceedings, pp. 1175-1178.*

* cited by examiner

*Primary Examiner* — Long V Le
*Assistant Examiner* — Katherine McDonald
(74) *Attorney, Agent, or Firm* — Rosenberg, Klein & Lee

(57) ABSTRACT

An image generation system is provided, the system generating an ultrasound image and a photo-acoustic image of an object and including a dual-wavelength laser source, an optical filter, and an optical-based ultrasound sensor. The laser source generates a first laser pulse with a first wavelength or a second laser pulse with a second wavelength. The optical filter almost completely absorbs the energy of the first laser pulse and by the photo-acoustic effect, generates and transmits an ultrasound to the object so the object scatters and reflects the ultrasound. The second laser pulse almost completely penetrates the optical filter and is transmitted to the object so the object absorbs the energy of the second laser pulse, generates and sends a photo-acoustic signal. The optical-based ultrasound sensor receives the ultrasound and the photo-acoustic signal to generate the ultrasound image and the photo-acoustic image of the object.

10 Claims, 8 Drawing Sheets

IMAGE GENERATION SYSTEM

This application claims the benefits of the Taiwan Patent Application Serial NO. 102101627 filed on Jan. 16, 2013, the subject matter of which is incorporated herein by reference.

BACKGROUND OF THE INVENTION

1. Field of the Invention

The present invention relates to an image generation system and more particularly, relates to an image generation system switching between dual-wavelength lasers, outputting the laser to an optical filter and generating an ultrasound image and a photo-acoustic image of an object by a photo-acoustic effect.

2. Description

The technique of generating images by means of ultrasound has been widely adopted in biomedical applications. Compared with other medical imaging systems such as X-ray, computed tomography (CT), magnetic resonance imaging (MRI) and nuclear medicine imaging utilized in clinic, ultrasonic imaging has advantages of cost effectiveness, non-invasiveness, no ionizing radiation, real-time imaging capability, high spatial resolution (less than 1 millimeter), portability, flow estimation ability, etc. Thus, ultrasound imaging has been commonly applied to clinical diagnosis in several medical categories.

Apart from ultrasound imaging, the photo-acoustic effect has also been utilized in imaging; photo-acoustic effect means when an object is exposed to light, the object absorbs the energy of light and then thermal expansion effect happens within a short period of time; sound waves are thus generated. One purpose of photo-acoustic imaging is to show the distribution of optical absorption of the object by receiving the sound waves.

At present, both ultrasound imaging and photo-acoustic imaging utilize a receiving device in an ultrasound probe to receive sound waves for subsequent image processing. However, due to some clinical and medical needs, making probes more compact and smaller has been an important development task. For example, the need for endoscopic and intravascular imaging has been a driving force to develop miniaturized ultrasound probes.

When developing miniaturized probes for ultrasound imaging, piezoelectric materials such as Lead Zirconate Titanated (PZT) are often used. However, when it comes to miniaturization, it is very difficult to cut ceramic piezoelectric materials. Meanwhile, crosstalk interference is more likely to happen which makes developing miniaturized probes more difficult.

SUMMARY OF THE INVENTION

When developing miniaturized probes for ultrasound imaging, piezoelectric materials such as Lead Zirconate Titanated (PZT) are needed. However, when it comes to micro-miniaturizing, it is very difficult to cut piezoelectric materials; meanwhile, crosstalk interference also happens in circuit layouts among components, which makes developing miniaturized probes more difficult.

Therefore, an image generation system is provided according to embodiments of the present invention. Under an optical design, the system switches between dual-wavelength lasers, and outputs the laser to an optical filter. An optical filter is utilized to select one of the two wavelengths, and thus an ultrasound image and a photo-acoustic image of an object can be respectively generated based on the wavelength.

Besides, an image generation system provided according to embodiments of the present invention receives sound waves generated during ultrasound imaging and photo-acoustic imaging with an optical-based ultrasound sensor; therefore, piezoelectric materials and front-end electronics are not needed.

An image generation system is provided according to embodiments of the present invention. The system generates an ultrasound image and a photo-acoustic image of an object; the system includes a dual-wavelength laser source, an optical filter and an optical-based ultrasound sensor. The laser source outputs a first laser pulse having a first wavelength or a second laser pulse having a second wavelength. The optical filter receives and filters the first laser pulse and the second laser pulse. The optical filter absorbs the energy of the first laser pulse, generates and transmits a photoacoustics-based ultrasound to the object; the object backscatters and reflects the photoacoustics-based ultrasound so an echo is generated; on the other hand, the second laser pulse penetrates the optical filter so the second laser pulse is transmitted to the object; the object absorbs laser energy of the second laser pulse to generate photo-acoustic wave. The optical-based ultrasound sensor receives the echo to generate the ultrasound image of the object and receives the photo-acoustic wave to generate the photo-acoustic image of the object.

Preferably, the optical-based ultrasound sensor includes a polymer microring resonator, the polymer microring including a one-dimensional array receiver or a two-dimensional array receiver. An input end of the optical-based ultrasound sensor is coupled to a continuous-wave tunable laser and an output end of the optical-based ultrasound sensor is coupled to an optical detector so as to detect an ultrasound waveform according to light intensity at the output end. The system further includes the optical detector, an AD converter and a signal processing device. The optical detector is utilized to measure the laser output of the optical based ultrasound sensor. The AD converter is electrically connected to the optical detector. The signal processing device is electrically connected to the AD converter. The optical detector detects the light intensity so as to generate and send an analog detection signal to the AD converter, and the AD converter digitalizes the analog detection signal and generates and sends a digital detection signal. The signal processing device receives, records and saves the digital detection signal and recoveries at least an ultrasound waveform or a waveform of photo-acoustic signal according to the light intensity of the output end of the polymer microring resonator.

The signal processing device is preferably a desktop computer, a notebook computer or a tablet computer. The optical filter absorbs the laser energy of the first laser pulse with a high absorption rate, and transmits the second laser pulse with a high transmission rate; the absorption rate and the transmission rate are selected from 90% to 100%. The system can further include a motor for mechanical scanning to obtain the whole image of the object. The laser source is selected from the group of a tunable pulsed laser, and an Nd:YAG laser coupled with a Ti:Sapphire laser. The optical filter is selected from the group of a low pass filter, a band pass filter and a high pass filter and it can be flexible to bend for geometric focusing.

Compared with prior art, the image generation system provided according to embodiments of the present invention switches between dual-wavelength lasers, outputs the laser to an optical filter, and the optical filter has higher absorption rate or transmission rate according to laser wavelengths, and thus an ultrasound image and a photo-acoustic image of an object is generated.

Besides, an image generation system provided according to embodiments of the present invention receives sound waves generated during ultrasound imaging and photo-acoustic imaging with the optical-based ultrasound sensor; therefore, piezoelectric materials and electrical circuits are not needed in the probes. When minimizing the ultrasound probe, concerns regarding cutting piezoelectric materials and crosstalk interference are unnecessary and thus it is beneficial for the development of miniaturized ultrasound probe.

BRIEF DESCRIPTION OF THE DRAWINGS

Other features and advantages of this invention will become more apparent in the following detailed description of the preferred embodiments of this invention, with reference to the accompanying drawings.

DETAILED DESCRIPTION OF THE PREFERRED EMBODIMENT

The present invention relates to an image generation system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
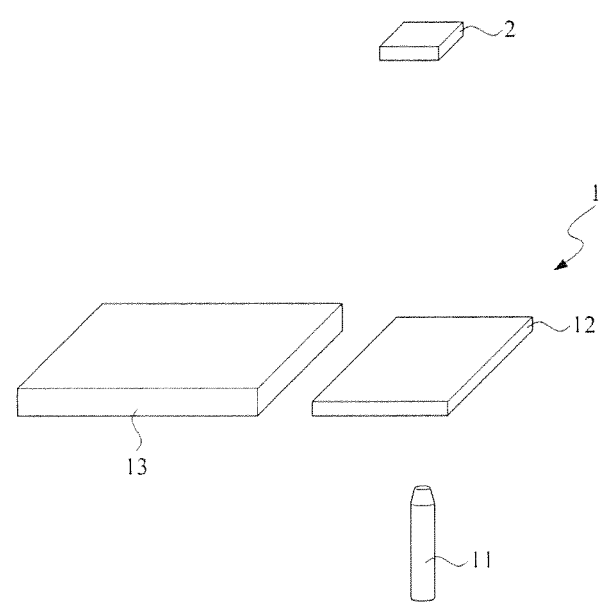
FIG. 1 is a schematic view of an image generation system according to a first embodiment of the present invention.

Refer to FIG. 1, a schematic view of an image generation system according to a first embodiment of the present invention. An image generation system 1 generates an image of an object 2, the image generation system 1 including a laser source 11, an optical filter 12 and an optical-based ultrasound sensor 13. The laser source 11 is selected from the group of a tunable pulsed laser, an Nd:YAG laser coupled with a Ti:Sapphire laser or other dual-wavelength laser source. According to the first embodiment of the present invention, the laser source 11 includes a tunable pulsed laser. The optical filter is selected from the group of a low pass filter, a band pass filter or a high pass filter.

The optical-based ultrasound sensor 13 is disposed close to the optical filter 12 side-by-side, front-to-rear, in layers, or in contrast (such as a microscope). According to the first embodiment of the present invention, the optical-based ultrasound sensor 13 is disposed side-by-side with the optical filter 12. The optical-based ultrasound sensor 13 includes a polymer microring resonator, the polymer microring including a one-dimensional array receiver or a two-dimensional array receiver. It should be noted that the object 2 is not limited in medical or clinical applications; any object of ultrasonic imaging or photo-acoustic imaging can be object 2.

Figure 2A:
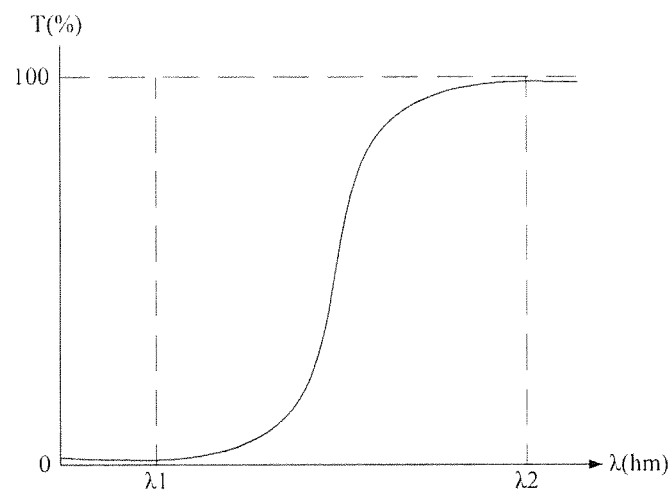
FIG. 2A is a spectrum showing a transmission rate of an optical filter of the first embodiment of the present invention transmitting a laser.
Figure 2B:
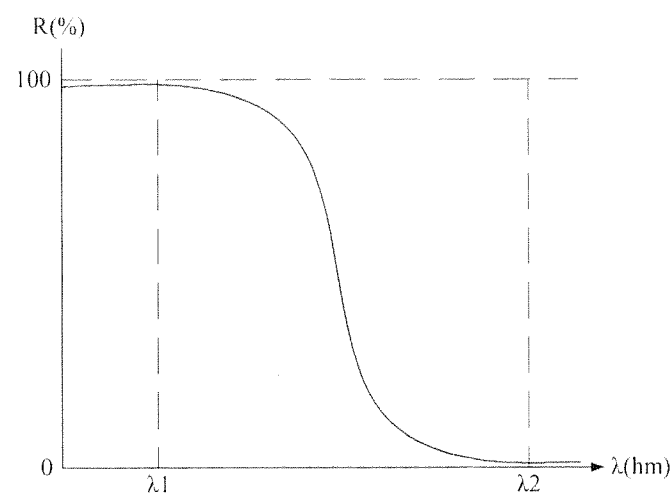
FIG. 2B is a spectrum showing an absorption rate of the optical filter of the first embodiment of the present invention absorbing a laser.

Refer to FIG. 1, FIG. 2A and FIG. 2B. FIG. 2A is a spectrum showing a transmission rate of an optical filter; FIG. 2B is a spectrum showing an absorption rate of the optical filter. The laser source 11 generates a first laser pulse (not shown) having a first wavelength λ1 or a second laser pulse (not shown) having a second wavelength λ2. According to the first embodiment of the present invention, since the laser source 11 includes a tunable pulsed laser, the laser source 11 adjusts and outputs the first laser pulse having the first wavelength λ1 or adjusts and outputs the second laser pulse having the second wavelength λ2.

The optical filter 12 absorbs and filters the first laser pulse and the second laser pulse. According to the first embodiment of the present invention, the optical filter 12 absorbs the first laser pulse with a high absorption rate from 90% to 100% (and transmits the first laser pulse with a transmission rate from 0% to 10%). That is, the optical filter 12 absorbs the first wavelength λ1 with the absorption rate from 90% to 100%. The first wavelength λ1 in the first embodiment of the present invention is a wavelength with an absorption rate close to 100% and a transmission rate close to 0% (as shown in FIGS. 2A and 2B).

According to the first embodiment of the present invention, the optical filter 12 transmits the second laser pulse with a transmission rate from 90% to 100% (and absorbs the second laser pulse with an absorption rate from 0% to 10%). That is, the optical filter 12 transmits the second wavelength λ2 with the transmission rate from 90% to 100%. The second wavelength λ2 in the first embodiment of the present invention is a wavelength with a transmission rate close to 100% and an absorption rate close to 0% (as shown in FIGS. 2A and 2B). According to the first embodiment of the present invention, the first wavelength λ1 is 532 nm and the second wavelength λ2 is 800 nm, which are selected correspondingly to the optical filter 12. Therefore, in other embodiments of the present invention, the first wavelength λ1 and the second wavelength λ2 can be within 532 nm to 800 nm or except from 532 nm to 800 nm, which should all depends on absorbing and transmitting features of the optical filter 12 and should not be limited within 532 nm to 800 nm. In other words, an Nd:YAG laser coupled with a Ti:Sapphire laser or a tunable pulsed laser can be applied in the first embodiment of the present invention to satisfy the needs of the wavelengths.

Figure 3:
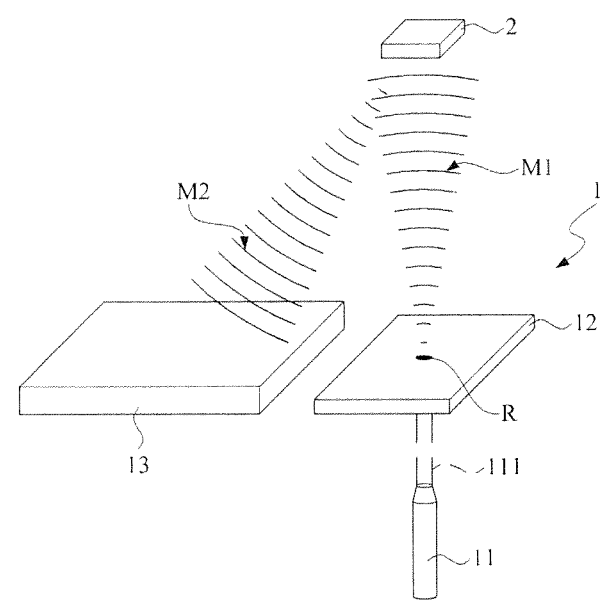
FIG. 3 is a schematic view showing imaging when the optical filter of the image generation system of the first embodiment of the present invention absorbing a first laser pulse.

Refer to FIGS. 2A, 2B and 3; FIG. 3 is schematic view showing imaging when the optical filter of the image generation system of the first embodiment of the present invention absorbing a first laser pulse. A user is to obtain an ultrasound image of the object 2 with the laser source 11 outputting a first laser pulse 111 having the first wavelength λ1 to the optical filter 12, the optical filter 12 almost completely absorbing the first laser pulse 111 with the absorption rate close to 100%. Since the absorption rate is close to 100%, a photo-acoustic effect is generated in an absorption area R of the optical filter 12 and a photoacoustics-based ultrasound M1 is generated and transmitted to the object 2; when the photoacoustics-based ultrasound M1 reaches the object 2, the object 2 scatters and reflects the photoacoustics-based ultrasound M1 so an echo M2 is generated; the echo M2 is received by the optical-based ultrasound sensor 13 (polymer microring resonator) so that the ultrasound image of the object 2 is obtained according to the echo M2 of the object 2.

Since the echo M2 is generated by the object 2 reflecting or scattering the photoacoustics-based ultrasound M1 transmitted to the object 2, the ultrasound image provides structural image of the object 2.

It should be noted that the imaging method described in FIG. 3 is ultrasound imaging, i.e. imaging of the object 2 based on its acoustic properties, and since the image processing after the optical-based ultrasound sensor 13 receiving the echo M2 belongs to prior art, it will not be mentioned redundantly here. Besides, the transmission ranges of the photoacoustics-based ultrasound M1 and the echo M2 are in fact wider and FIG. 3 is merely a schematic view.

Figure 4:
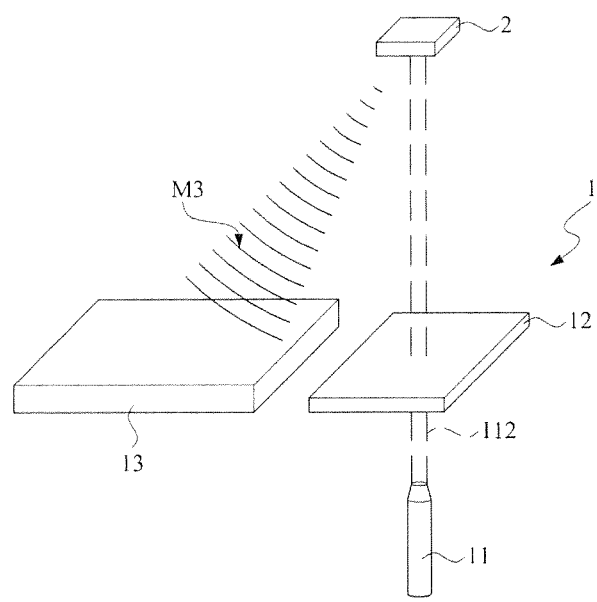
FIG. 4 is a schematic view showing imaging when the optical filter of the image generation system of the first embodiment of the present invention transmitting a second laser pulse.

Refer to FIGS. 2A, 2B and 4; FIG. 4 is schematic view showing imaging when the optical filter of the image generation system of the first embodiment of the present invention transmitting a second laser pulse. A user is to obtain a photo-acoustic image of the object 2 with the laser source 11 outputting the second laser pulse 112 having the second wavelength $\lambda 2$ to the optical filter 12, the optical filter 12 almost completely transmitting the second laser pulse 112 to the object 2 with the transmission rate close to 100%. Since the object 2 receives the energy of the second laser pulse 112, a photo-acoustic wave M3 is generated and transmitted to the optical-based ultrasound sensor 13 (polymer microring resonator) so that the photo-acoustic image of the object 2 is obtained according to the photo-acoustic wave M3 generated by the object 2.

It should be noted that the imaging method described in FIG. 4 is photo-acoustic imaging, i.e. imaging of the object 2 based on its optical properties, and since the image processing after the optical-based ultrasound sensor 13 receiving the photo-acoustic wave M3 belongs to prior art, it will not be mentioned redundantly here. Besides, the transmission range of the photo-acoustic wave M3 is in fact wider and FIG. 4 is merely a schematic view.

Figure 5:
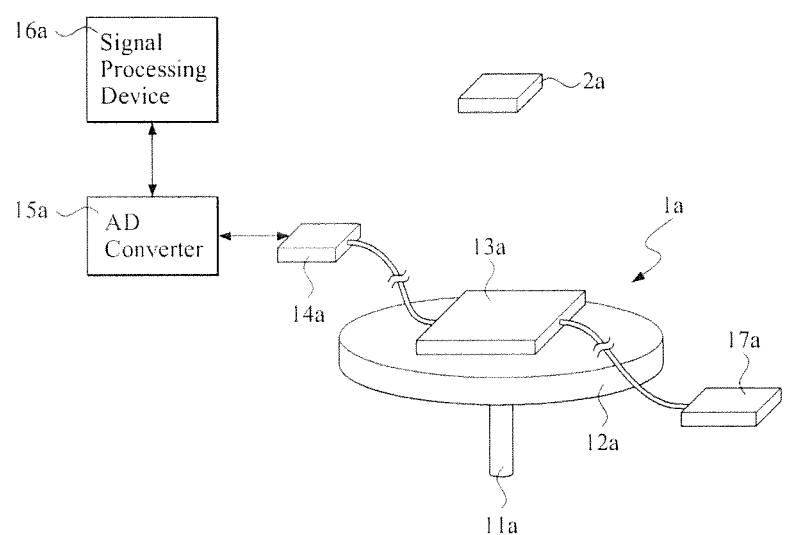
FIG. 5 is a schematic view of an image generation system according to a second embodiment of the present invention.

Refer to FIG. 5, a whole schematic view of an image generation system according to a second embodiment of the present invention. An image generation system 1a includes a laser source 11a, an optical filter 12a and an optical-based ultrasound sensor 13a, and further includes an optical detector 14a, an AD converter 15a and a signal processing device 16a, wherein the optical-based ultrasound sensor 13a is disposed on top of the optical filter 12a; the laser source 11a, the optical filter 12a and the optical-based ultrasound sensor 13a are the same with the first embodiment of the present invention and are not mentioned redundantly here. The optical detector 14a is coupled to an output end (not shown) of the optical-based ultrasound sensor 13a and an input end (not shown) of the optical-based ultrasound sensor 13a is coupled to a continuous wavelength tunable laser 17a. The continuous wavelength tunable laser 17a provides continuous optical signals so that the optical-based ultrasound sensor 13a measures an ultrasound waveform according to the light intensity detected by the optical detection device 14a. The AD converter 15a is electrically connected to the optical detection device 14a; the signal processing device 16a is electrically connected to the AD converter 15a, wherein the signal processing device 16a is selected from the group of a desktop computer, a notebook computer and a tablet computer.

The optical detector 14a detects the light intensity so as to generate and send an analog detection signal (not shown) to the AD converter 15a, and the AD converter 15a digitalizes the analog detection signal and generates and sends a digital detection signal (not shown). The signal processing device 16a receives the digital detection signal and rebuilds and saves at least an ultrasound waveform or a waveform of photo-acoustic signal according to the light intensity of the output end of the optical-based ultrasound sensor 13a.

According to other embodiments of the present invention, the image generation system 1a further includes a scanning motor (not shown) coupled to the laser source 11a, the optical filter 12a and the optical-based ultrasound sensor 13a, the scanning makes 2D or 3D imaging of an object 2a possible. More specifically, the image generation system 1a includes an integrated ultrasound/photo-acoustic imaging probe coupled with a scanning motor and the imaging system; further the scanning motor drives mechanical scanning and fetches the ultrasound image and the photo-acoustic image individually.

Figure 6:
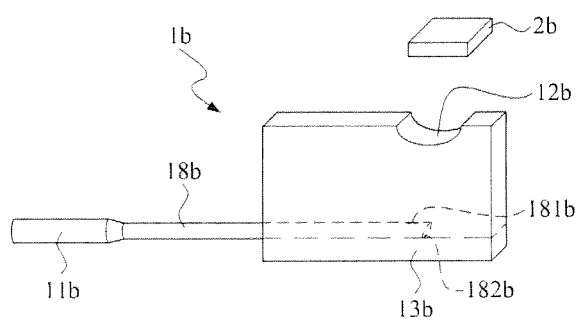
FIG. 6 is a schematic view of an image generation system according to a third embodiment of the present invention.

Refer to FIG. 6, a schematic view of an image generation system according to a third embodiment of the present invention. An image generation system 1b includes a portable ultrasound probe, the system including a laser source 11b, an optical filter 12b, an optical-based ultrasound sensor 13b and further an optical fiber 18b, wherein the optical filter 12b is flexible and is disposed as a concave; besides, the optical filter 12b is disposed on an upper surface of the housing (not shown) and the optical-based ultrasound sensor 13b is disposed inside the bottom of the housing. The optical fiber 18b is coupled to the laser source 11b and penetrates through the housing; the optical fiber 18b includes a light emitting end 181b and an end 182b; the end 182b includes a skew angle (the angle between the surface of the light emitting end 181b and the surface of the end 182b is less than 90 degrees) so that when the laser source 11b outputs a first laser pulse (not shown) or a second laser pulse (not shown), the two laser pulses are transmitted in the optical fiber 18b, reflected by the skew angle of the end 182b and outputted to the optical filter 12b via the light emitting end 181b. The description of the rest of the third embodiment is the same as the description of the FIG. 3 and FIG. 4. According to the third embodiment of the present invention, the optical filter 12b is disposed as a concave—this is to focus the photoacoustics-based ultrasound with the geometrical characteristic of a concave so as to improve the imaging resolution of the ultrasound imaging.

Figure 7:
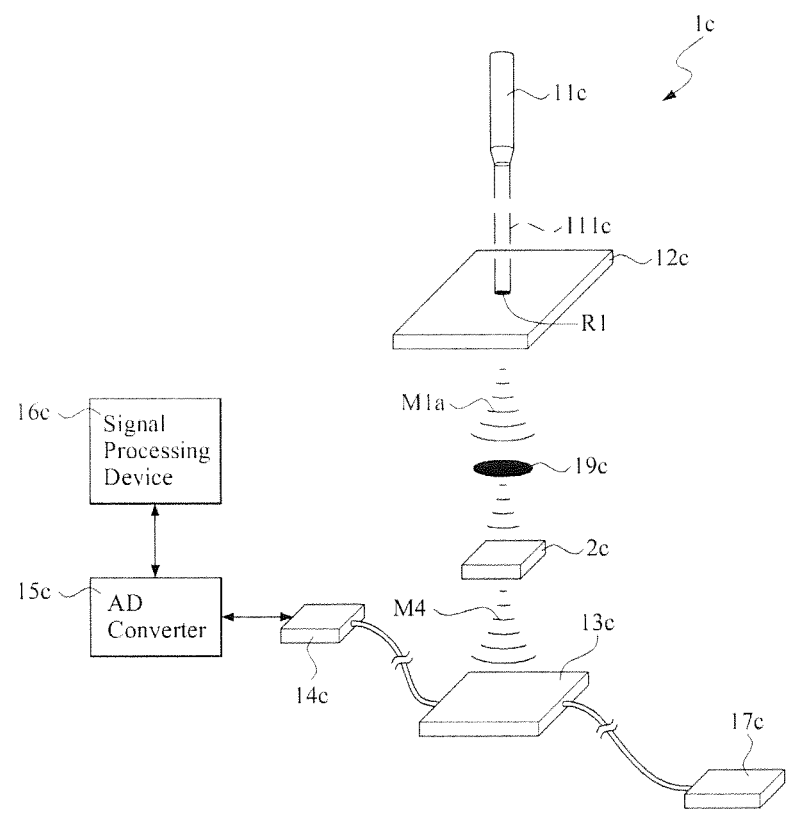
FIG. 7 is a schematic view showing imaging when the optical filter of the image generation system of a fourth embodiment of the present invention absorbing a first laser pulse.

Refer to FIG. 7, a schematic view showing imaging when the optical filter of the image generation system of a fourth embodiment of the present invention absorbing a first laser pulse. An image generation system 1c is utilized in an ultrasonic microscope (not shown), the system including a laser source 11c, an optical filter 12c, an optical-based ultrasound sensor 13c, an optical detector 14c, an AD converter 15c, an electronic processing device 16c, a continuous wavelength tunable laser 17c and further a lens 19c. The lens 19c is selected from the group of an optical lens and an ultrasonic lens for both acoustic and optical focusing.

According to the fourth embodiment of the present invention, the laser source 11c outputs a first laser pulse 111c having the first wavelength $\lambda 1$ to the optical filter 12c. The optical filter 12c almost completely absorbs the first laser pulse 111c. Since the absorption rate is close to 100%, a photo-acoustic effect is generated in an absorption area R1 of the optical filter 12c and a photoacoustics-based ultrasound M1a is generated and transmitted to an object 2c; the photoacoustics-based ultrasound M1a is focused on the surface of the object 2c via the lens 19c and a scattered and reflected ultrasound M4 is generated on the object 2c and transmitted to the optical-based ultrasound sensor 13c so that an ultrasonic microscope image of the object 2c is obtained.

Figure 8:
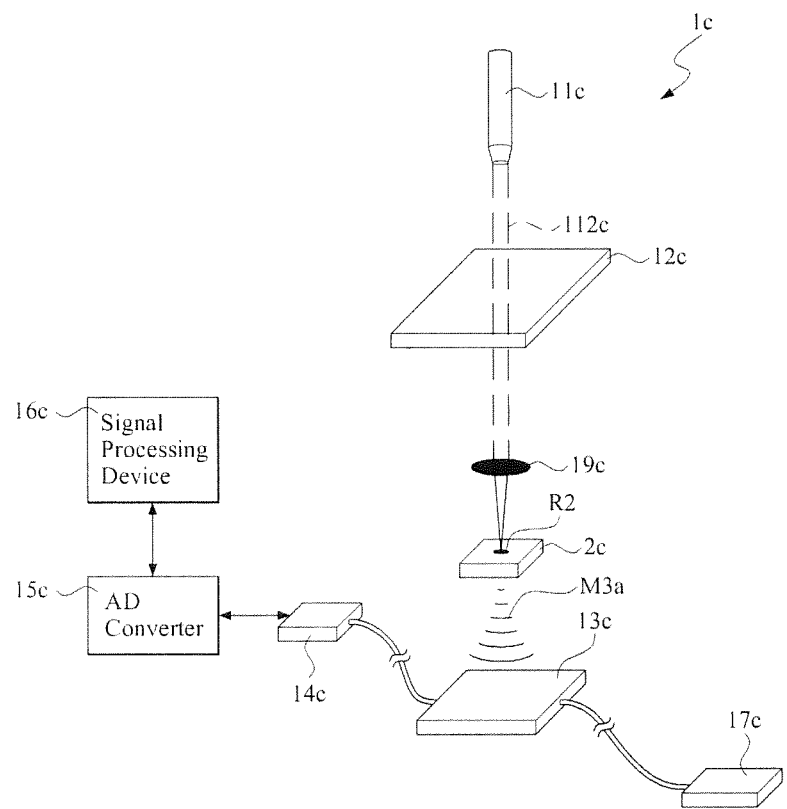
FIG. 8 is a schematic view showing imaging when the optical filter of the image generation system of the fourth embodiment of the present invention transmitting a second laser pulse.

Refer to FIG. 8, a schematic view showing imaging when the optical filter of the image generation system of the fourth embodiment of the present invention transmitting a second laser pulse. The image generation system 1c is utilized in an ultrasonic/photoacoustic microscope. When a user is to obtain a photo-acoustic microscope image of the object 2c, the laser source 11c outputs a second laser pulse 112c having the second wavelength λ2 to the optical filter 12c, the optical filter 12c almost completely transmitting the second laser pulse 112c to the lens 19c so as to focus the laser onto the object 2c with the transmission rate close to 100%. Since the object 2c receives the energy of the second laser pulse 112c, a photo-acoustic wave M3a is generated and transmitted to the optical-based ultrasound sensor 13c so that the photo-acoustic image of the object 2c is obtained according to the photo-acoustic wave M3a. According to the fourth embodiment of the present invention, the image generation system 1c includes the optical and ultrasonic lens 19c to focus the ultrasound and light; other features are the same as mentioned in other embodiments of the present invention and therefore are not mentioned redundantly here.

In conclusion, the image generation system provided according to embodiments of the present invention receives sound waves generated during ultrasound imaging and photo-acoustic imaging with the optical-based ultrasound sensor; therefore, piezoelectric materials are not needed. When minimizing the ultrasound probe, concerns regarding cutting piezoelectric materials and crosstalk interference are unnecessary and thus it is beneficial for the development of miniaturized ultrasound probe. Besides, since the ultrasound probe manufactured according to embodiments of the present invention can be minimized effectively, the development of one-dimensional array or even two-dimensional array is improved so as to replace mechanical scanning and increase the speed of imaging.

While the present invention has been particularly shown and described with reference to a preferred embodiment, it will be understood by those skilled in the art that various changes in form and detail may be without departing from the spirit and scope of the present invention.

What is claimed is:

1. An image generation system, the system generating an ultrasound image and a photo-acoustic image of an object, the system comprising:
    a laser source outputting a first laser pulse having a first wavelength and a second laser pulse having a second wavelength;
    an optical filter receiving and filtering the first laser pulse and the second laser pulse, the optical filter almost completely absorbing the energy of the first laser pulse, generating and transmitting a photoacoustics-based ultrasound to the object, the object scattering and reflecting the photoacoustics-based ultrasound so an echo is generated; the optical filter almost completely transmitting the second laser pulse so the second laser pulse is transmitted to the object, the object scattering and reflecting a photo-acoustic wave; and
    an optical-based ultrasound sensor disposed close to the optical filter, the optical-based ultrasound sensor receiving the echo to generate the ultrasound image of the object and receiving the photo-acoustic wave to generate the photo-acoustic image of the object.

2. The system according to claim 1, wherein the optical-based ultrasound sensor includes a polymer microring resonator, the polymer microring including a one-dimensional array receiver or a two-dimensional array receiver.

3. The system according to claim 1, further comprising an optical detector and an AD converter, wherein the optical detector is coupled to an output end of the optical-based ultrasound sensor and the AD converter is electrically connected to the optical detector, the optical detector detecting the light intensity of the output end of the optical-based ultrasound sensor so as to generate and send an analog detected signal to the AD converter, the AD converter digitalizing the analog detected signal so as to generate and send a digital detected signal.

4. The system according to claim 1, further comprising a continuous wavelength tunable laser coupled to an input end of the optical-based ultrasound sensor.

5. The system according to claim 3, further comprising a signal processing device electrically connected to the AD converter, the signal processing device receiving the digital detected signal and recovering at least an ultrasound waveform or a waveform of photo-acoustic signal.

6. The system according to claim 5, wherein the signal processing device is selected from the group of a desktop computer, a notebook computer and a tablet computer.

7. The system according to claim 1, wherein the optical filter absorbs the first laser pulse with a high absorption rate and transmits the second laser pulse with a high transmission rate; the absorption rate and the transmission rate are selected from 90% to 100%.

8. The system according to claim 1, further comprising a scanning motor coupled to the laser source, the optical filter and the optical-based ultrasound sensor, the scanning makes 2D or 3D image of the object.

9. The system according to claim 1, wherein the laser source is selected from the group of a tunable pulsed laser, and an Nd:YAG laser coupled with a Ti:Sapphire laser.

10. The system according to claim 1, wherein the optical filter is selected from the group of a low pass filter, a band pass filter and a high pass filter.

* * * * *